(12) United States Patent
Prasad et al.

(10) Patent No.: US 10,309,956 B2
(45) Date of Patent: Jun. 4, 2019

(54) PROCESS FOR ASSESSING RISK OF SUBSTANCE ADMINISTRATION

(71) Applicant: R. J. Reynolds Tobacco Company, Winston-Salem, NC (US)

(72) Inventors: Gaddamanugu L. Prasad, Winston-Salem, NC (US); Subhashini Arimilli, Winston-Salem, NC (US)

(73) Assignees: R.J. Reynolds Tobacco Company, Winston-Salen; Wake Forest University Health Sciences, Winston-Salen ( * ) Notice: Subject to any disclaimer, the term of this patent is extended or adjusted under 35 U.S.C. 154(b) by 0 days.

(21) Appl. No.: 14/796,091

(22) Filed: Jul. 10, 2015

(65) Prior Publication Data
US 2016/0025705 A1 Jan. 28, 2016

Related U.S. Application Data

(60) Provisional application No. 62/022,757, filed on Jul. 10, 2014.

(51) Int. Cl.
*G01N 33/53* (2006.01)
*G01N 33/50* (2006.01)

(52) U.S. Cl.
CPC ..... *G01N 33/5023* (2013.01); *G01N 33/5047* (2013.01); *G01N 2800/50* (2013.01)

(58) Field of Classification Search
CPC ............... G01N 33/5023; G01N 33/5047
See application file for complete search history.

(56) References Cited

U.S. PATENT DOCUMENTS

| 9,009,675 B2 | 4/2015 | Corthesy et al. |
| 9,558,318 B2 | 1/2017 | Hoeng et al. |
| 2014/0172398 A1 | 6/2014 | Hoeng et al. |

OTHER PUBLICATIONS

Jorgensen et al., (Cell Cycle. Sep. 2004.3:9;1154-1168).*
VanLeeuwen et al., (Toxicological Sciences. Apr. 13, 2005. 86(1);2000-2010).*
Gao et al, (BMC Genomics. May 11, 2010;11:292, 25 pages).*
Hecht (Nat Reviews Cancer. Oct. 2003:3;733-744).*
Weinberg et al., (Clin Vaccine Immunol. Aug. 2009;16(8):1176-86. Epub Jun. 10, 2009).*
Corning Inc., General Guide for Cryogenically Storing Animal Cell Cultures. 2004 (10 pages).*
Mian et al., (Mol Immunol. Sep. 2009;46(15):3108-16.Epub Jul. 9, 2009).*
Arimilli, Subhashini et al.; Methods to Evaluate Cytotoxicity and Immunosuppression of Combustible Tobacco Product Preparations; Journal of Visualized Experiments; dated Jan. 10, 2015.
Arimilli, Subhashini et al.; Rapid isolation of Leukocyte Subsets from Fresh and Cryopreserved Peripheral Blood Mononuclear Cells in Clincal Research; Cryoletters, vol. 33, No. 5, dated Sep. 2012.

* cited by examiner

*Primary Examiner* — Prema M Mertz
(74) *Attorney, Agent, or Firm* — Middleton Reutlinger

(57) ABSTRACT

A process for assessing risk that administration of a substance will suppress immune competence in a population of subjects is provided. Such a substance may be a substance related to, contained in or derived from a tobacco product or, more generally, a substance concerning which it is desired to assess risk of administration of the substance.

17 Claims, No Drawings

PROCESS FOR ASSESSING RISK OF SUBSTANCE ADMINISTRATION

FIELD

A process such as is described in various embodiments herein relates to a process for assessing risk that administration of a substance will suppress immune competence in a population of subjects. Such a substance may be a substance related to, contained in or derived from a tobacco product or, more generally, a substance concerning which it is desired to assess risk of suppressing immune competence upon administration of the substance.

BACKGROUND

An exogenous substance provided to an individual may affect the functions of components of innate immunity, including natural killer (NK) cells and T lymphocytes. NK cells are a vital part of the innate immune system and play an important role against microbial infections and tumor surveillance through secretion of an array of cytokines including IFN-γ (Interferon-γ) and TNF-α (Tumor Necrosis Factor-α) and by cytolysis of infected or neoplastic cells. Toll-Like Receptors (TLRs) are involved in innate immunity by recognizing molecules that are broadly shared by pathogens, and they activate a cascade of signaling pathways, triggering NF-κB and type-1 interferon production. T cells are involved in the initiation and regulation of innate and adaptive immune responses. T cell subsets play specific roles in eliciting an immune response. Exposure to or administration of an exogenous substance may decrease CD4/CD8 cell ratios and alter T cell function including cytokine secretion and proliferation.

Substances such as cigarette smoke extracts may inhibit the secretion of cytokines such as IL-1β (Interluekin-1β), IL-2 (Interluekin-2), IFN-γ and TNF-α by Peripheral Blood Mononuclear Cells (PBMCs). Such proinflammatory cytokines are capable of driving NK cell and cytotoxic T cell responses that are critical to tumor suppression. Given the importance of these cell types in the immune response, it has been suggested that T cell and NK cell response resulting from smoking could significantly impair the ability to fight viral and bacterial infections as well as tumor surveillance.

While cigarette smoking has represented a most common form of tobacco consumption, non-combustible tobacco such as, moist snuff, snus, and other smoke-free products, also exist in the marketplace. Relative to cigarettes, health risks associated with the use of smokeless tobacco products have typically been shown to be lower.

The effect of cigarette smoking on immune function has been the subject of considerable research, but less is known of how the use of non-combustible forms of tobacco, including smokeless tobacco, electronic cigarettes or nicotine, may alter the immune response. For example, some in vitro studies suggest smokeless tobacco elicits immunostimulatory responses as observed by altered cytokine secretion. There has accordingly been a long-felt need for a process for assessing risk that a substance, such as a component substance of a tobacco product, will suppress immune competence in a population of subjects.

Cigarette smoke consists of a particulate phase and a gas-vapor phase. The particulate phase, dissolved in dimethyl sulphoxide (DMSO) (or alternate solvent) is known as Total Particulate Matter (TPM) and is commonly used in cell culture studies. A different method of exposing cells to cigarette smoke involves the use of smoke-conditioned medium generated by passing cigarette smoke through it; this preparation is referred to as cigarette smoke extract, whole smoke conditioned medium (WS-CM) or other types of aqueous extracts. Each of these Tobacco Product Preparations (TPPs) is chemically distinct and therefore could elicit different responses. Alternatively, whole smoke may be exposed to cells directly. Smokeless tobacco (ST) extracts may be generated in several different ways: for example, direct extraction in cell culture medium or extraction in complete artificial saliva (CAS) or other solvents.

It has been an open question how combustible and non-combustible TPPs modulate select immune responses in a population of subjects. There has accordingly been a long-felt need for a process for assessing risk that a substance, such as a combustible or non-combustible TPP, will suppress immune competence in a population of subjects.

SUMMARY OF EMBODIMENTS

A process such as is described in various embodiments herein provides, inter alia, a process for assessing risk that administration of a substance will suppress immune competence in a population of subjects, the process comprising: collecting a sample of blood from each a plurality of subjects, said subjects being members of the population; isolating peripheral blood mononuclear cells (PBMCs) from the sample of blood to form isolated PBMCs; administering the substance to the isolated PBMCs or isolated subpopulations of PBMCs, such as NK cells and Cytotoxic T cells (CD8+ T cells), thereby forming substance-exposed PBMCs or subpopulations of PBMCs; stimulating the substance-exposed PBMCs or subpopulations of PBMCs with a Toll-like receptor (TLR) ligand to form TLR-ligand stimulated substance-exposed PBMCs or subpopulations of PBMCs or stimulating with phorbol 12-myristate 13-acetate (PMA) and Ionomycin (Iono) which is a general stimulator to form PMA/Ionomycin stimulated substance-exposed PBMCs or subpopulations of PBMCs; measuring one or more responses of effector cells in the Toll-like receptor-ligand stimulated substance-exposed PBMCs or subpopulations of PBMCs or PMA/Ionomycin stimulated substance-exposed PBMCs or subpopulations of PBMCs to form one or more measured responses; aggregating the one or more measured responses from each of the plurality of subjects to form one or more response aggregates; comparing the one or more response aggregates to one or more immune-competence-associated reference ranges, thereby assessing risk that administration of the substance will suppress immune competence in the population of subjects.

When used in connection with a process such as is described in various embodiments herein, the term "subject" may denote an animal. For example, a subject may be an animal such as a mouse. For example, a subject may be a human being.

When used in connection with a process such as is described in various embodiments herein, the term "aggregating" may denote compiling and/or storing and/or summarizing data. For example, collecting data and preparing one or more summary statistics, such as a mean, a median, a mode, a standard deviation, a standard error of the mean, and/or a range from the collected data is an instance of aggregating. Accordingly, an "aggregate" may denote one or more summary statistics, including, for example, one or more measures of central tendency and/or one or more measures of spread. An "aggregate" may denote a nonparametric statistic.

DETAILED DESCRIPTION

A process such as is described in various embodiments herein now will be described more fully hereinafter. A process such as is described in various embodiments herein may, however, be embodied in many different forms and should not be construed as limited to the embodiments set forth herein; rather, these embodiments are provided so that this disclosure will be thorough and complete, and will fully convey the scope of a process such as is described in various embodiments herein to those skilled in the art. As used in this specification and the claims, the singular forms "a," "an," and "the" include plural referents unless the context clearly dictates otherwise.

A process such as is described in various embodiments herein provides, inter alia, a process for assessing risk that administration of a substance will suppress immune competence in a population of subjects, the process comprising: collecting a sample of blood from each a plurality of subjects, said subjects being members of the population; isolating peripheral blood mononuclear cells (PBMCs) from the sample of blood to form isolated PBMCs; administering the substance to the isolated PBMCs, thereby forming substance-exposed PBMCs; stimulating the substance-exposed PBMCs with a Toll-like receptor ligand to form Toll-like receptor-ligand stimulated substance-exposed PBMCs; or stimulating with phorbol 12-myristate 13-acetate (PMA) and Ionomycin (Iono) which is a general stimulator to form PMA/Iono stimulated substance-exposed PBMCs; measuring one or more responses of effector cells in the Toll-like receptor-ligand stimulated substance-exposed PBMCs or PMA/Iono stimulated substance-exposed PBMCs to form one or more measured responses; aggregating the one or more measured responses from each of the plurality of subjects to form one or more response aggregates; comparing the one or more response aggregates to one or more immune-competence-associated reference ranges, thereby assessing risk that administration of the substance will suppress immune competence in the population of subjects.

Embodiments of a process such as is described in various examples herein are more fully illustrated such as may follow below, set forth to illustrate a process such as is described and not to be construed as limiting thereof.

In an embodiment, TPPs were prepared as follows. TPM was prepared by smoking 3R4F reference cigarettes using the standard ISO method (35 mL, 60 s, 2 s; puff volume, frequency and duration, respectively) and dissolving the particulate phase, trapped on the Cambridge filter pad, in DMSO. Smokeless tobacco extract was prepared by extracting 2S3 reference smokeless tobacco (ST) (North Carolina State University Tobacco Services Analytical Laboratory) for 2 h in complete artificial saliva (CAS) using a published method. The CAS consists of mucin, salts (potassium chloride, sodium chloride, calcium chloride dehydrate, dipotassium hydrogen phosphate and magnesium chloride hexahydrate), urea, glucose and enzymes (alpha-amylase, lysozyme and acid phosphatase). WS-CM was prepared by passing smoke from four 3R4F cigarettes through 20 mL of RPMI 1640 medium (Invitrogen, Grand Island, N.Y.) without phenol red. Nicotine free base (Sigma-Aldrich, Milwaukee, Wis.) was used as a reference. Aliquots of fresh or frozen TPPs were analyzed for nicotine, tobacco specific nitrosamines (TSNAs) and polycyclic aromatic hydrocarbons (PAHs) at Labstat International (Kitchener, Ontario, Canada) using published methods. TPPs and nicotine were tested at different doses based on the equi-nicotine unit paradigm. The $EC_{50}$ values of different TPPs were determined by 7-aminoactinomycin D (7AAD) positive staining of PBMCs on flow cytometer. The $EC_{50}$ is defined as the concentration at which 50% of the cells were no longer viable in a 24 h assay and the values are expressed as µg of equi-nicotine units/mL. The $EC_{50}$ values of combustible preparations TPM and WS-CM were determined to be 2.58 µg/mL and 1.56 µg/mL of equi-nicotine units, respectively. As discussed in a previous publication, $EC_{50}$ values for non-combustible ST/CAS could not be determined due to its low cytotoxicity, which required addition of substantial (>30%) volumes of ST/CAS into cell culture medium. Separately, CAS at higher volumes altered basal and TLR ligand-induced immune responses which interfered with the assessment of the effects of treatment at higher doses of ST/CAS. Hence, results are presented with ST/CAS at 2 µg/mL of equi-nicotine units, which is comparable to the dose used for combustible TPPs. The nicotine $EC_{50}$ value was determined to be 1650 µg/mL. A range of lower doses of TPPs and nicotine were also used. Equivalent volumes of media, DMSO and CAS were used as controls for WS-CM, TPM and ST/CAS, respectively.

Isolation of PBMCs and subpopulations of PBMCs was performed as described in the inventors' previous publication (Rapid isolation of leukocyte subsets from fresh and cryopreserved peripheral blood mononuclear cells in clinical research. Arimilli et al., (2012), Cryo Letters 33 (5) 376-384). Briefly, fresh blood was collected from healthy adult donors (who did not consume any tobacco products) by a local clinical contract research organization (PMG Research, Winston-Salem, N.C.). Written informed consent was obtained from all volunteers and the protocol was approved by an Institutional Review Board (IRB). PBMCs were isolated by standard density gradient centrifugation using Isolymph® (CTL Scientific Supply Corp., Deer Park, N.Y.). Isolated PBMCs were cryopreserved for further use.

Isolation of NK cells can be performed by taking approximately 50 million isolated PBMCs mixed with 100 µL of CD56 microbeads and incubated for 15 minutes as per the Miltenyi Biotec (Auburn, Calif.) protocol. After washing the PBMC/bead mixture with running buffer (Miltenyi Biotec, Auburn, Calif.), they were passed through AutoMACS cell separator to yield purified NK cells.

Isolation of CD8 cytotoxic T lymphocytes can be performed using similar methodology. For example, $50 \times 10^6$ isolated PBMCs are mixed with 100 µL of CD8 microbeads and incubated for 15 minutes. After washing the PBMC/bead mixture with running buffer the cells are passed through AutoMACS cell separator to yield purified cytotoxic Cd8 T cells. Purity of the CD56 or Cd8 cells can be checked by flow cytometer by labeling the cells with CD56-PE antibody or CD8-PerCP antibody respectively. The method describes the use of a set of commercial reagents, and other commercial/in-house developed reagents and equipment can be used.

PBMCs were treated with different concentrations (nicotine units) of WS-CM, TPM, ST/CAS and neat nicotine for 3 h in a 24-well plate at 3 million cells/well in 2 mL RPMI complete media. Dosing was based on an equi-nicotine exposure paradigm. Cells were washed after 3 h treatment and re-plated in a 48-well plate at 1 million cells/well/mL with and without the presence of 10 µg/mL polyinosinic:polycytidylic acid (poly I:C) or lipopolysaccharide (LPS). After a 67 h incubation, supernatants were taken for secreted cytokine analysis. Cells were plated onto a 96-well plate at $1 \times 10^6$/mL and further incubated for 4 h with 200 µL of media with Golgiplug (1 µg/mL) (BD Biosciences, San Jose, Calif.) to measure intracellular cytokines. Cells were then harvested, washed and surface stained for CD56-PE and CD2-FITC, CD69-APC monoclonal antibodies (mAB) for 30 min at 4° C. After washing, cells were fixed and permeabilized with BD Biosciences Cytofix/Cytoperm buffer for 20 min on ice in the dark. Cells were then stained with anti-IFN-γ-PE, anti-TNF-α-APC and anti-perforin-FITC mAB and incubated for an additional 30 min on ice. After washing the cells, they were re-suspended in a total volume of 200 μL of 2% paraformaldehyde for FACS analysis. Forward scatter, side scatter, fluorescence intensity and percent positivity were measured after acquiring 100,000 cells per sample by flow cytometry (BD Biosciences, San Jose, Calif.), and the data were analyzed using Cell Quest (BD Biosciences, San Jose, Calif.) and Flow Jo (Tree Star, Ashland, Oreg.) software.

The inventors have established conditions appropriate for such an assay. Previous methods utilized stimulation with TLR agonists (LPS is for TLR-2 and Poly I:C is for TLR3) for 67 h to measure intracellular cytokines and secreted cytokines. A time-course of cytokine secretion in TLR-stimulated cells (under control conditions with no TPPs) suggested that maximal secretion occurred at 24 h (Methods to evaluate cytotoxicity and immunosuppression of combustible tobacco product preparations. Arimilli et al., Journal of Visualized Experiments. 2015 Jan. 10; (95):52351). Furthermore, the inventors further established assay conditions by combining TLR agonist $(LPS)^+$ PMA/Ion$^+$Golgiplug and reduced the time of incubation to a total of 6 h for measuring optimal intracellular cytokines. Similarly the inventors measured optimal secreted cytokines by incubating TLR agonist $(LPS)^+$ PMA/Ion for 24 h. Thus, these modifications led to substantially reduced assay times and improved the ex vivo assay.

PBMC culture supernatants were harvested after 67 h of poly I:C or LPS stimulation from the above experiments or 24 h from the modified protocol. A Cytometric Bead Array (CBA) for human cytokine secretion was used. Measured were IL-1β, IL-6, IL-8, IL-10, IL-12, and TNF-α (BD Biosciences, San Jose, Calif.) by flow cytometry according to the manufacturer's instructions. Among the TPPs tested, WS-CM exerted a profound inhibitory effect (which was statistically significant, P<0.0005) on the secretion of the cytokines. Levels of IL-1β, IL-6, IL-10 and TNF-α were profoundly reduced in WS-CM-treated PBMCs stimulated with poly I:C or LPS. While IL-8 and IL-12 secretion was reduced by 94% and 68% with poly I:C, respectively, they were reduced by 91% and 67% with LPS, respectively. Treatment with TPM also reduced the secretion of several cytokines upon stimulation with the TLR ligands. Statistically significant reductions were observed in IL-10 (>60%), IL-12 (>68%) and TNF-α (>80%) secretion with both TLR ligands. TPM also suppressed IL-1β and IL-6 levels in LPS-stimulated cells. Pre-treatment with ST/CAS resulted in statistically significant reductions in IL-6 levels with poly I:C, but not with LPS stimulation.

Suppression of TNF-α$^+$ and IFN-γ$^+$ T cell populations in PBMCs treated with TPPs. It was sought to evaluate intracellular cytokine levels in T cells after treating with combustible and non-combustible TPPs. In a first set of experiments, measured was the induction of intracellular TNF-α and IFN-γ by flow cytometry after PBMCs were treated with TPPs and stimulated with either poly I:C or LPS. Stimulation with TLR ligands resulted in robust and statistically significant increases in TNF-α$^+$ and IFN-γ$^+$ cells compared to unstimulated controls (basal).

It was assessed whether the pretreatment of PBMCs with TPPs compromised their ability to produce TNF-α$^+$ cells when stimulated with poly I:C and LPS. TPPs by themselves induced basal number of TNF-α$^+$ T cells. A dose-dependent suppression of TNF-α$^+$ T cells in stimulated PBMCs by WS-CM was evident. Although a 26% reduction from control with WS-CM at 0.5 μg/mL was detected, a statistically significant reduction in number of TNF-α$^+$ T cells (72%) was observed at 1.56 μg/mL of equi-nicotine units of WS-CM. Treatment with TPM did not result in statistically significant differences at the doses tested. Treatment with ST/CAS at 2 μg/mL of equi-nicotine units did not alter the number of TNF-α producing T cells. T cells treated with nicotine (10-1650 μg/mL) did not yield statistically significant differences in their TNF-α$^+$ T cell numbers to poly I:C and LPS stimulation. Exposure to 1650 μg/mL of nicotine resulted in higher basal levels of TNF-α$^+$ T cells, which were unaltered by stimulation with the TLR ligands.

Evaluated also were changes in the number of IFN-γ$^+$ T cells with TPP treatment followed by poly I:C and LPS stimulation. The TPPs induced a minimal number of IFN-γ$^+$ T cells under basal (non-stimulated) conditions. Control and DMSO treated cells showed an increase in the number of IFN-γ$^+$ T cells after poly I:C and LPS induction. Treatment with WS-CM resulted in near complete suppression of IFN-γ$^+$ T cells induced by poly I:C and LPS, while incubation with TPM resulted in a statistically significant dose dependent reduction of IFN-γ$^+$ T cells. In terms of equi-nicotine units, the combustible TPPs, WS-CM and TPM, were far more potent suppressors of IFN-γ$^+$ T cells than ST/CAS or nicotine. Treatment with combustible TPPs resulted in statistically significant suppression of IFN-γ$^+$ T cells at or below 2.58 μg/mL of equi-nicotine units. Measurable suppression of the cytokine-positive cells was observed only at the highest concentrations of nicotine, although these changes were not statistically significant. Thus, a dose-dependent suppression of IFN-γ$^+$ T cells in response to TPM treatment was observed, whereas WS-CM was more potent in suppressing TNF-α$^+$ and IFN-γ$^+$ T cells at both doses tested. The combustible TPPs exerted more pronounced effects relative to ST/CAS and nicotine. Furthermore, IFN-γ$^+$ T cells appeared to be compromised more severely by combustible TPPs and nicotine (1650 μg/mL) than TNF-α$^+$ T cells in the stimulated PBMCs.

Suppression of TNF-α$^+$ NK cell populations in PBMCs treated with TPPs. Because of the importance of NK cells in innate immunity, tested was the effect of TPPs on the induction of TNF-α$^+$ NK cells in poly I:C- and LPS-stimulated PBMCs. Consistent with the data obtained with T cells, NK cells treated with WS-CM showed the lowest number of TNF-α$^+$ NK cells after stimulation with poly I:C and LPS when compared to the control cells. The inhibition of TNF-α$^+$ NK cells was more pronounced with combustible TPPs than ST/CAS at equi-nicotine units (WS-CM>TPM>ST/CAS). PBMCs treated with WS-CM showed 90% reduction and TPM showed 64% reduction of intracellular TNF-α$^+$ NK cells, which were statistically significant, upon stimulation with TLR ligands. However, pretreatment with ST/CAS did not result in statistically significant changes relative to vehicle control. While pretreatment with lower doses (10 and 500 μg/mL) of nicotine did not induce statistically significant changes in TNF-α$^+$ NK cells, pretreatment at a higher dose (1650 μg/mL) produced a statistically significant reduction after LPS stimulation.

Effect of TPPs on CD69 expression in NK cells. Since the induction of TNF-α$^+$ NK cells is reduced by TPPs in the stimulated NK cells, further investigated was whether TPPs interfered with NK cell differentiation and function. CD69 is an early inducible cell surface glycoprotein expressed during lymphoid activation and is involved in NK cell function. PBMCs were treated with TPPs, and CD69 expression on NK cell population was analyzed by flow cytometry after poly I:C and LPS stimulation. Pre-treatment of PBMCs with the TPPs resulted in increased CD69 expression upon stimulation with poly I:C and LPS. It is interesting to note that the WS-CM treatment increased CD69 expressing NK cells under basal conditions by 5-fold, whereas poly I:C or LPS did not further enhance CD69 expression. Exposure to nicotine (1650 µg/mL) did not increase the basal levels of the induction of CD69 relative to the untreated cells.

Suppression of PBMC cell target killing ability. As the intracellular and secreted cytokines are suppressed by pre-treatment with TPPs to varying degrees, it was tested whether the functional properties, particularly target cell killing by NK cells and $CD8^+$ T cells in the PBMC pool, were compromised from the exposure to TPPs. These two cell types are known as cytolytic effector cells that confer innate protection against viral and bacterial infections and are involved in anti-tumor surveillance. The K562 cell line was used as a target in a cytolytic assay. K562 cells were purchased from ATCC (Manassas Va., USA) and grown in RPMI complete media. One vial of cryopreserved PBMCs was thawed and washed, and a live cell count was taken. Different concentrations of TPPs were prepared in 100 µL media. $1.5 \times 10^6$ PBMCs in a 50 µL volume were added to each well and incubated for 1.5 h at 37° C. in 96-well round bottom plates. K562 target cells were labeled with carboxy fluorescein succinimidyl ester (CFSE) and added at a density of 100,000 cells/well (target:effector ratio is 1:15). Cell co-cultures were incubated at 37° C. for an additional 4 h. Immediately after the incubation period, cells were stained with 7AAD (which labels the dead cells) and the killing of CFSE-labeled K562 target cells was evaluated after 7AAD staining by flow cytometric analysis (BD Biosciences, San Jose, Calif.). Flow data were analyzed using Flow Jo software (Tree Star, Ashland, Oreg.). The cytolytic data on multiple donor PMBCs showed a statistically significant decrease of K562 cell killing ability with WS-CM (65%) treatment. Treatment with ST/CAS or nicotine did not reduce the target cell killing ability.

Effect of TPP exposure on perforin levels in total PBMCs and NK cells. It was investigated whether the altered cytolytic activity of PBMCs and NK cells is due to differences in the endogenous perforin levels. Perforin, a cytoplasmic granular protein, is known to mediate target cell killing. Therefore were determined perforin levels in TPP-treated PBMCs and NK cells. WS-CM-treated PBMCs and NK cells showed a statistically significant reduction (70% and 78%, respectively) in perforin levels. Treatment with TPM, ST/CAS and nicotine did not result in statistically significant changes in perforin levels in PBMC populations or NK cells.

The results were aggregated as the mean±the standard error of the mean (four donor samples). The t-test between treatment and untreated control samples was performed using Sigma Plot (version 9) or Excel software for all treatments with their corresponding controls.

In an embodiment, a process is provided for assessing the degree to which the exposure of combustible and non-combustible TPPs influences immune responses; particularly induction, secretion of cytokines and cytolytic activity by PBMCs. Cigarette smoking has been known to elicit inflammation and alter a wide range of innate and adaptive immune responses. Such altered immune responses have been linked to compromised host defense against microbial infections and tumor surveillance.

In an aspect, it was determined that exposure to combustible TPPs (WS-CM and TPM), on an equi-nicotine unit basis, caused potent immunosuppression relative to ST and nicotine, as measured by NK cell and T cell functions. Due to their critical role in modulating immune functions in response to microbial pathogens and in tumor surveillance, NK cells and T cells have been studied for possible adverse effects of smoking. For the first time, the effects of exposure to combustible and non-combustible TPPs were comparatively evaluated in a single system, addressing a long-felt need. Utilized was a well-characterized TLR stimulated PBMC system to assess the cellular and cytokine secretion in response to TPP exposure. Further to address a long-felt need, reported were the biological responses in equi-nicotine units for comparison of the effects of TPPs.

In an embodiment, to measure the effect of exposure to WS-CM and nicotine, PBMCs were treated with different concentrations of WS-CM and nicotine 3 h or 24 h. Cell death measured by 7-Aminoactinomycin D (7AAD) staining method is simple and more reliable as 7AAD intercalates into double-stranded nucleic acids and can penetrate cell membranes of dying or dead cells. A dose-dependent increase of cell death was observed with WS-CM at 24 h, with a near 80% cell death detected at 4 µg/mL of equi-nicotine units. A comparable degree of cell death was noted only at 3,000 µg/mL nicotine. Since PBMCs were exposed for 3 h with WS-CM and nicotine to assess their effect of cytokine induction and ability to kill target cells, it was reasonable to determine whether WS-CM caused significant cytotoxicity at 3 h treatment. PBMCs treated with 5 µg/mL of equi-nicotine units of WS-CM did not experience significant toxicity (<5%). Treatment with nicotine for 3 h caused measurable (8%) cell death only at 2000 µg/mL. Thus, exposure to WS-CM at the indicated doses and treatment periods did not cause significant cytotoxicity.

To measure immunomodulatory effects, PBMCs were stimulated with LPS for different time periods and the secreted cytokines were measured by cytometric bead array (CBA) method. To establish LPS stimulation time, PBMCs were exposed to LPS stimulation for 4 h, 24 h, 48 h and 72 h and secreted cytokines were measured. For example, LPS stimulation for 24 h yielded maximal secretion of cytokines IL-6 and IL-8, and extended time periods did not result in further increases (IL-6) or decreases (IL-8) in cytokine secretion. Similar results were obtained with other secreted cytokines such as IL-10, IL-1β and TNF-α.

Pilot time course experiments suggested that maximal production of cytokines, in responses to TLR-4 stimulation by LPS occurs at 24 h, and hence secreted cytokines were measured at 24 h in subsequent experiments. Treatment with WS-CM and nicotine, followed by stimulation of TLR-4 receptor with LPS, resulted in a dose-dependent decrease of secreted cytokines. Treatment with WS-CM resulted in profound decreases of IFN-γ, TNF, IL-10 and IL-6 at low equi-nicotine units (1.56 µg/mL).

Suppression of cytokines was also evident with nicotine. However, at significantly higher doses and the degree of suppression varied among individual cytokines. For example, IFN-γ appeared to be significantly suppressed with nicotine at a range of concentrations up to 500 µg/mL of nicotine, whereas IL-6 was suppressed at highest concentration (4 mg/mL) tested. Next were measured IL-8 levels in the same samples as above using an ELISA assay. IL-8 secretion was effectively suppressed in WS-CM treated PBMCs, while nicotine's suppressive effects were significant at 2 mg/mL.

In an example, intracellular cytokine levels in WS-CM and nicotine treated cells upon stimulation with LPS were measured. Previously PBMCs were stimulated for 3 days and Golgiplug was added in the last 4 h of incubation to measure intracellular cytokines. The incubation period was significantly reduced by combining stimulation with LPS and Golgiplug to total 6 h and measured intracellular cytokine-positive cells. This treatment yielded a dose-dependent percent reduction in IFN-γ-positive cells, TNF-α-positive cells and MIP-1α-positive cells. In this assay was observed a decrease in the number of intracellular cytokine-positive cells after exposure to WS-CM at lower nicotine units (1.56 μg/mL). Both secreted cytokine and intracellular cytokine assays showed similar results in terms of IFN-γ levels or IFN-γ-positive cells.

As a functional measure, determined was the ability of WS-CM and nicotine-treated PBMCs to kill target K562 cells. Treatment with WS-CM at 1.56 μg/mL significantly reduced the killing ability of the effector cells in PBMCs compared to control and the lower doses. Nicotine treatment at low and high doses did not interfere with the cell killing.

It has been demonstrated that treatment of PBMCs with TPPs suppresses several responses, including expression and secretion of cytokines and functional measures such as target cell killing. Experimental methods known in the art may require longer incubation periods.

Isolation of viable PBMCs is a key requirement for these ex vivo assays. Given the individual variability and physiological status in potential donors, it is ideal to obtain PBMCs that are responsive. For the purpose of this study, PBMCs were isolated from generally healthy adult subjects using a previously published method. Further, in this study to minimize variability among donors, excluded were those with allergies, infections or taking any prescriptions or over the counter drugs such as Aspirin.

Previous methods utilized stimulation with TLR agonists for 67-72 h to measure intracellular cytokines and secreted cytokines. A time-course of cytokine secretion in TLR stimulated cells (under control conditions with no WS-CM or nicotine) suggested that maximal secretion occurred at 24 h. Surprisingly favorable results were obtained when the duration of incubation with TLR agonists and Golgiplug was decreased to a total of 6 h for measuring intracellular cytokines. While this required a separate assay to measure cytokine-positive cells, the data are more robust compared to the previous method. Consistent with the previous results, WS-CM strongly suppressed the induction of intracellular and secreted cytokines. Thus, these modifications led to substantially reduced assay times and yielded results comparable to those described in literature.

Historically, target cell killing by effector PBMCs utilized radiolabeled methods (for example, a $^{51}Cr$ release assay). A process such as described herein does not require the use of radioactivity, and employs loading cells with a fluorescent dye whose presence was monitored by flow cytometry. Since the total length of incubation of the target cells with the effector cells was 5 h, it can be completed in about 8 h and can be adapted to high-throughput assays. In the art have been used longer methods with respect to the K562 killing assay involving cell subset isolation and activation/stimulation over a period of several days, or analyzing NK cell and K562 cell conjugates to monitor cytotoxic interactions. A process such as is described herein may utilize cryopreserved PBMCs directly as effector cells, which affords greater flexibility.

A process such as is described herein may provide any of several assays to determine the effect of TLR-mediated immune response in TPP-treated PBMCs, which can be readily applied for testing any of a variety of different compounds. The use of cryopreserved cells allows for significant flexibility, and together with the established techniques such as flow cytometry, CBA assays and ELISAs, robust and consistent results could be obtained rapidly across different laboratories.

In an embodiment, a substance may comprise a substance derived from a tobacco product. A substance may comprise a novel composition. A substance may comprise a composition obtained from the environment.

In an embodiment, a subject may be a human being. In an embodiment, a subject may be a rodent. In an embodiment, a subject may be a rat. In an embodiment, a subject may be a mouse. Accordingly, in an embodiment, a population of subjects may be a population of human beings, when the subject is a human being. A population of subjects may be a population of rodents, when the subject is a rodent.

In an embodiment, PBMCs may be cryopreserved. In an embodiment, PBMCs may be freshly obtained.

In an embodiment, administering a substance to PBMCs may comprise contacting the substance with the PBMCs.

In an embodiment, a Toll-like receptor ligand may comprise a bacterial lipopolysaccharide or other ligands.

In an embodiment, one or more responses of effector cells may comprise production of one or more cytokines. In an embodiment, one or more responses of effector cells may comprise a measured steady-state level of one or more cytokines.

Many modifications and other embodiments of a process such as is described in various embodiments herein will come to mind to one skilled in the art to which this invention pertains having the benefit of the teachings presented in the foregoing description. For example, one can utilize fresh TPPs or frozen TPPs, or sophisticated systems such as air-liquid interface systems of smoke exposure to treat cells. The methodology for preparation of different tobacco products also could be variable. Further, in addition to/instead of PBMCs, one can employ isolated NK cells (CD56) or cytotoxic (CD8) T cells to measure immune responses. Similarly, additional cytokines (intracellular or secreted) could be used to measure the effect of immune suppression/stimulation of cells. Alternatively, one can vary the dose, time of stimulation with TLR ligands and/or PMA/Ion, TPPs or employ a different technique to measure cellular responses. Therefore, it is to be understood that a process such as is described in various embodiments herein is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:
1. A process for assessing risk that administration of a tobacco product preparation (TPP) substance derived from tobacco will suppress immune competence in a population of subjects, the process comprising:
   collecting a sample of blood from each a plurality of subjects, said subjects being members of the population;

isolating peripheral blood mononuclear cells (PBMCs) from the sample of blood to form isolated PBMCs;

administering the TPP substance to the isolated PBMCs for 3 hours, thereby forming substance-exposed PBMCs;

stimulating the substance-exposed PBMCs with a Toll-like receptor ligand to form Toll-like receptor-ligand stimulated substance-exposed PBMCs, wherein the stimulating takes place for a duration of less than 6 hours;

measuring one or more levels of a cytokine in the Toll-like receptor-ligand stimulated substance-exposed PBMCs to form one or more measured responses;

aggregating the one or more measured responses from each of the plurality of subjects to form one or more response aggregates;

comparing the one or more response aggregates to one or more immune-competence-associated reference ranges measured in control cells, thereby assessing risk that administration of the substance will suppress immune competence in the population of subjects.

2. The process according to claim 1, wherein the substance derived from tobacco comprises total particulate matter.

3. The process according to claim 1, wherein the tobacco product is a smokeless tobacco product.

4. The process according to claim 1, wherein the stimulating takes place for a duration of no more than 5 hours.

5. The process according to claim 1, wherein the cytokine is TNF-α.

6. The process according to claim 1, wherein the cytokine is IFN-γ.

7. The process according to claim 1, wherein the cytokine is IL-1β.

8. The process according to claim 1, wherein the cytokine is IL-10.

9. The process according to claim 1, wherein the cytokine is IL-12.

10. The process according to claim 1, wherein the Toll-like receptor ligand comprises a bacterial lipopolysaccharide.

11. The process according to claim 1, wherein the Toll-like receptor ligand comprises polyinosinic:polycytidylic acid (Poly I:C).

12. The process according to claim 1, additionally comprising administering phorbol 12-myristate 13-acetate (PMA) and Ionomycin (Iono) (PMA/Iono) to the substance-exposed PBMCs.

13. A process for assessing risk that administration of a tobacco product preparation (TPP) substance derived from tobacco will suppress immune competence in a population of subjects, the process comprising:

collecting a sample of blood from each a plurality of subjects, said subjects being members of the population;

isolating peripheral blood mononuclear cells (PBMCs) from the sample of blood to form isolated PBMCs;

administering the TPP substance derived from tobacco to the isolated PBMCs for 3 hours, thereby forming substance-exposed PBMCs;

stimulating the substance-exposed PBMCs with phorbol 12-myristate 13-acetate (PMA) and Ionomycin (Iono) to form PMA/Iono stimulated substance-exposed PBMCs, wherein the stimulating takes place for a duration of less than 6 hours;

measuring one or more responses of levels of a cytokine in the PMA/Iono stimulated substance-exposed PBMCs to form one or more measured responses;

aggregating the one or more measured responses from each of the plurality of subjects to form one or more response aggregates;

comparing the one or more response aggregates to one or more immune-competence-associated reference ranges measured in control cells, thereby assessing risk that administration of the substance will suppress immune competence in the population of subjects.

14. A process for assessing risk that administration of a tobacco product preparation (TPP) substance derived from tobacco will suppress immune competence in a population of human subjects, the process comprising:

collecting a sample of blood from each a plurality of human subjects, said subjects being members of the population;

isolating peripheral blood mononuclear cells (PBMCs) from the sample of blood to form isolated PBMCs;

administering the TPP substance to the isolated PBMCs for 3 hours, thereby forming substance-exposed PBMCs;

stimulating the substance-exposed PBMCs with a Toll-like receptor ligand to form Toll-like receptor-ligand stimulated substance-exposed PBMCs, wherein the stimulating takes place for a duration of less than 6 hours;

measuring one or more levels of a cytokine in the Toll-like receptor-ligand stimulated substance-exposed PBMCs to form one or more measured responses;

aggregating the one or more measured responses from each of the plurality of subjects to form one or more response aggregates;

comparing the one or more response aggregates to one or more immune-competence-associated reference ranges measured in control cells, thereby assessing risk that administration of the substance will suppress immune competence in the population of human subjects.

15. A process for assessing risk that administration of a tobacco product preparation (TPP) substance derived from tobacco will suppress immune competence in a population of human subjects, the process comprising:

collecting a sample of blood from each a plurality of human subjects, said subjects being members of the population;

isolating peripheral blood mononuclear cells (PBMCs) from the sample of blood to form isolated PBMCs;

administering the TPP substance to the isolated PBMCs for 3 hours, thereby forming substance-exposed PBMCs;

stimulating the substance-exposed PBMCs with PMA/Iono stimulated substance-exposed PBMCs, wherein the stimulating takes place for a duration of less than 6 hours;

measuring one or more levels of a cytokine in the PMA/Iono stimulated substance-exposed PBMCs to form one or more measured responses;

aggregating the one or more measured responses from each of the plurality of subjects to form one or more response aggregates;

comparing the one or more response aggregates to one or more immune-competence-associated reference ranges measured in control cells, thereby assessing risk that administration of the substance will suppress immune competence in the population of human subjects.

16. A process for assessing risk that administration of a tobacco product preparation (TPP) substance derived from tobacco will suppress immune competence in a population of subjects, the process comprising:
  collecting a sample of blood from each a plurality of subjects, said subjects being members of the population;
  isolating peripheral blood mononuclear cells (PBMCs) from the sample of blood to form isolated PBMCs;
  cryopreserving the isolated PBMCs at temperature less than zero degrees Celsius;
  warming the isolated PBMCs to a temperature higher than zero degrees Celsius;
  administering the TPP substance to the isolated PBMCs for 3 hours, thereby forming substance-exposed PBMCs;
  stimulating the substance-exposed PBMCs with a Toll-like receptor ligand to form Toll-like receptor-ligand stimulated substance-exposed PBMCs, wherein the stimulating takes place for a duration of less than 6 hours;
  measuring one or more levels of a cytokine in the Toll-like receptor-ligand stimulated substance-exposed PBMCs to form one or more measured responses;
  aggregating the one or more measured responses from each of the plurality of subjects to form one or more response aggregates;
  comparing the one or more response aggregates to one or more immune-competence-associated reference ranges measured in control cells,
thereby assessing risk that administration of the substance will suppress immune competence in the population of subjects.

17. A process for assessing risk that administration of a tobacco product preparation (TPP) substance derived from tobacco will suppress immune competence in a population of subjects, the process comprising:
  collecting a sample of blood from each a plurality of subjects, said subjects being members of the population;
  isolating peripheral blood mononuclear cells (PBMCs) from the sample of blood to form isolated PBMCs;
  cryopreserving the isolated PBMCs at temperature −150 degrees Celsius;
  warming the isolated PBMCs to a temperature 37 degrees Celsius;
  administering the TPP substance to the isolated PBMCs for 3 hours, thereby forming substance-exposed PBMCs;
  stimulating the substance-exposed PBMCs with PMA/Iono to form stimulated substance-exposed PBMCs, wherein the stimulating takes place for a duration of less than 6 hours;
  measuring one or more levels of a cytokine in the PMA/Iono stimulated substance-exposed PBMCs to form one or more measured responses;
  aggregating the one or more measured responses from each of the plurality of subjects to form one or more response aggregates;
  comparing the one or more response aggregates to one or more immune-competence-associated reference ranges measured in control cells,
thereby assessing risk that administration of the substance will suppress immune competence in the population of subjects.

* * * * *